(12) United States Patent
Goud et al.

(10) Patent No.: US 6,613,882 B1
(45) Date of Patent: Sep. 2, 2003

(54) CHIMERIC POLYPEPTIDE COMPRISING THE FRAGMENT B OF SHIGA TOXIN AND PEPTIDES OF THERAPEUTIC INTEREST

(75) Inventors: Bruno Goud, Paris (FR); Ludger Johannes, Paris (FR)

(73) Assignee: Institut Curie and Centre National de la Recherche Scientifique, Paris (FR)

( * ) Notice: Subject to any disclaimer, the term of this patent is extended or adjusted under 35 U.S.C. 154(b) by 0 days.

(21) Appl. No.: 09/484,471

(22) Filed: Jan. 18, 2000

Related U.S. Application Data

(63) Continuation of application No. PCT/FR98/01573, filed on Jul. 17, 1998.

(30) Foreign Application Priority Data

Jul. 18, 1997 (FR) .............................................. 97 09185

(51) Int. Cl.$^7$ ........................ C07K 19/00; A61K 38/00; A61K 39/00

(52) U.S. Cl. ........................ 530/350; 514/2; 424/184.1

(58) Field of Search .............................. 530/387.1, 300, 530/350; 424/236.1, 184.1; 514/2

(56) References Cited

FOREIGN PATENT DOCUMENTS

| EP | 439 954 | 8/1991 |
|---|---|---|
| WO | WO 93/16186 | 8/1993 |
| WO | WO 93/17115 | 9/1993 |
| WO | WO 97/13410 | 4/1997 |

OTHER PUBLICATIONS

Lee, et al., 1998, Eur. J. Immunol., 28:2726–2737.*
Johannes, et al., 1997, J. Biol. Chem., 272:19554–61.*
Johannes, et al., 1996, Molec Biol of the Cell 7(Supp):75a.*
Allinquant, B et al. "Downregulation of Amyloid Precursor Protein Inhibits Neurite Outgrowth In Vitro," *J. Cell Biol.* 128(5):919–27 (1995).
Boël, Pascale, et al. "BAGE: a New Gene Encoding an Antigen Recognized on Human Melanomas by Cytolytic T Lymphocytes," *Immunite* 2:167–75 (1995).
Bower, Stanley et al. "Cloning and Characterization of the *Bacillus subtilis* birA Gene Encoding a Repressor of the Biotin Operon," *J. Bacteriology* 177(9):2572–75 (1995).
Brichard, Vincent et al. "The Tyrosinase Gene Codes for an Antigen Recognized by Autologous Cytolytic T Lymphocytes on HLA–A2 Melanomas," *J. Exp. Med.* 178:489–95 (1993).
Calderwood, Stephen B. et al. "Nucleotide sequence of the Shiga–like toxin genes of *Escherichia coli*," *Proc. Natl. Acad. Sci. USA* 84(13):4364–68 (1987).
Chicz, Roman M. et al. "Analysis of MHC–presented peptides: applications in autoimmunity and vaccine development," *Immunol. Today* 15(4):155–60 (1994).

Ciernik, I. Frank et al. "Mutant Oncopeptide Immunization Induced CTL Specifically Lysing Tumor Cells Endogenously Expressing the Corresponding Intact Mutant p53," *Hybridoma* 14(2):139–42 (1995).
Coulie, Pierre G. et al. "A New Gene Coding for a Differentiation Antigen Recognized by Autologous Cytolytic T Lymphocytes on HLA–A2 Melanomas," *J. Exp. Med.* 180:35–42 (1994).
Davis, Heather L. et al. "DNA–Mediated Immunization in Mice Induces a Potent MHC Class I–Restricted Cytotoxic T Lymphocyte Response to the Hepatitis B Envelope Protein," *Hum. Gene Therapy* 6:1447–56 (1995).
De Plaen, Etienne et al. "Structure, chromosomal localization, and expression of 12 genes of the MAGE family," *Immunogenetics* 40:360–69 (1994).
Feltkamp, Mariet C. W. et al. "Vaccination with cytotoxic T lymphocyte epitope–containing peptide protects against a tumor induced by human papillomavirus type 16–transformed cells," *Eur. J. Immunol.* 23:2242–49 (1993).
Furukawa, Keiko et al. "Clonal Expansion of CD8$^+$ Cytotoxic T Lymphocytes against Human T Cell Lymphotrophic Virus Type I (HTLV–I) Genome Products in HTLV–I–associated Myelopathy/Tropical Spastic Paraparesis Patients," *J. Clin. Invest.* 94:1830–39 (1994).
Gnjatic, Sacha et al. "Mapping and ranking of potential cytotoxic T epitopes in the p53 protein: effect of mutations and polymorphism on peptide binding to purified and refolded HLA molecules," *Eur. J. Immunol.* 25:1638–42 (1995).
Johannes, Ludger et al. "Retrograde Transport of KDEL––bearing B–fragment of Shiga Toxin," *J. of Biological Chemistry* 272(31):19554–19561 (1997).
Johannes, L. and Goud, B., "Shiga toxin as a tool to study retrograde transport," *Molecular Biology of the Cell* 7(Supp.):75a (1996) (Annual Meeting of the 6$^{th}$ International Congress of Cell Biology and the 36$^{th}$ American Society for Cell Biology, San Francisco, California).

(List continued on next page.)

Primary Examiner—Anthony C. Caputa
Assistant Examiner—Misook Yu
(74) *Attorney, Agent, or Firm*—Lahive & Cockfield, LLP; Giulio A. DeConti, Jr.; Cynthia M. Soroos

(57) ABSTRACT

The invention pertains to chimeric polypeptides of the formula:

Figure 1A:
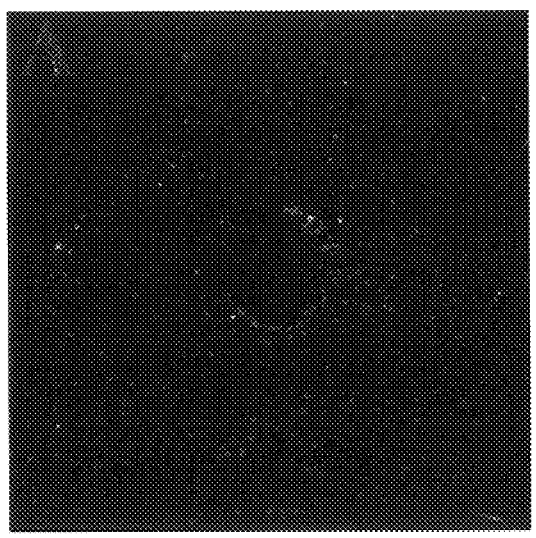

B—X wherein B represents the B fragment of Shiga toxin or a functional equivalent thereof, and X represents one or more polypeptides of therapeutic significance. Compositions for therapeutic use comprising the polypeptide B—X are also included.

12 Claims, 5 Drawing Sheets

OTHER PUBLICATIONS

Kawakami, Yutaka et al. "Identification of the Immunodominant Peptides of the MART–1 Human Melanoma Antigen Recognized by the Majority of HLA–A2–restricted Tumor Infiltrating Lymphocytes," *J. Exp. Med.* 180:347–52 (1994).

Kim, Jae Hong et al. "Dynamic Measurement of the pH of the Golgi Complex in Living Cells Using Retrograde Transport of the Verotoxin Receptor," *J. Cell Biol.* 134(6):1387–99 (1996).

Lamb, "Nucleotide sequence of cloned cDN coding for preproricin," *Eur. J. of Biochem.* 148(2):265–70 (1995).

Lewis, Michael L. and Pelham, Hugh R. B. "A human homologue of the yeast HDEL receptor," *Nature* 348:162–63 (1990).

Lewis, Michael J. and Pelham, Hugh R. B. "Ligand–Induced Redistribution of a Human KDEL Receptor from the Golgi Complex to the Endoplasmic Reticulum," *Cell* 68:353–64 (1992).

Lingwood, Clifford A. "erotoxins and Their Glycolipid Recetpros," *Adv. Lipid Res.* 25:189–211 (1993).

Murray, R. J. et al. "Identification of Target Antigens for the Human Cytotoxic T Cell Response to Epstein–Barr Virus (EBV): Implications for the Immune Control of EBV–positive Malignancies," *J. Exp. Med.* 176:157–68 (1992).

O'Brien, A. D. et al. "Shiga Toxin: Biochemistry, Genetics, Mode of Action, and Role in Pathogenesis," *Curr. Top. Microbiol. Immunol.* 180:65–94 (1992).

Peace, David J. et al. "Induction of T Cells Specific for the Mutated Segment of Oncogenic P21–$^{ras}$protein by Immunization In Vivo with the Oncogenic Protein," *J. Immunotherapy* 14(2):110–14 (1993).

Pelham, Hugh R. B. et al. "Toxin entry: how reversible is the secretory pathway?" *Trends Cell Biol.* 2:183–85 (1992).

Rapak, Andrzej et al. "Retrograde transport of mutant ricin to the endoplasmic reticulum with subsequent translocation to the cytosol," *Proc. Natl. Acad. Sci. USA* 94:3783–3788 (1997).

Rehermann, Barbara et al. "The Cytotoxic T Lymphocyte Response to Multiple Hepatitis B Virus Polymerase Epitopes During and After Acute Viral Hepatitis," *J. Exp. Med.* 181:1047–58 (1995).

Sandvig, Kirsten et al. "Retrograde Transport from the Golgi complex to the ER of Both Shiga Toxin and the Nontoxic Shiga B–gragment Is Regulated by Butryric Acid and cAMP," *J. Cell. Biol.* 126(1):53–64 (1994).

Sandvig, Kirsten et al. "Retrograde transport of endocytosed Shiga toxin to the endolasmic reticulum," *Nature* 358:510–12 (1992).

Seidah, Nabil G. et al. "Complete Amino Acid Sequence of Shigella Toxin B–chain," *J. Biol. Chem.* 261(30):13928–31 (1986).

Strockbine, Nancy A. et al. "Cloning and Sequencing of the Genes for Shiga Toxin from *Shigella dysenteriae* Type 1," *J. Bacteriology* 170(3):1116–22 (1988).

Suk, Guo–Fu et al. "Construction of Stable LamB–Shiga Toxin B Subunit Hybrids: Analysis of Expression in *Salmonella typhimurium* aroA Strains and Stimulation of B Subunit–Specific Mucosal and Serum Antibody Responses," *Infection and Immunity* 60:3345–59 (1992).

Traversari, Catia et al. "A Nonapeptide Encoded by Human Gene MAGE–1 Is Recognized on HLA–A1 by Cytolytic T Lymphocytes Directed against Tumor Antigen MZ2–E," *J. Exp. Med.* 176:1453–57 (1992).

Tsao, Kwei–Lan et al. "A Versatile plasmid expression vector for the production of biotinylated proteins by site–specific, enzymatic modification in *Escherichia coli,"* *Gene* 169:59–64 (1996).

Van den Eynde, Benoît et al. "A New Family of Genes Coding for an Antigen Recognized by Autologous Cytoloic T Lymphocutes on a Human Melanoma," *J. Exp. Med.* 182:689–98 (1995).

* cited by examiner

CHIMERIC POLYPEPTIDE COMPRISING THE FRAGMENT B OF SHIGA TOXIN AND PEPTIDES OF THERAPEUTIC INTEREST

This is a continuation of PCT/FR 98/01573, filed Jul. 17, 1998.

The invention relates to means and to their use for intracellular transport of proteins or polypeptides, also to the membrane presentation of certain epitopes.

Retrograde transport can be defined as the movement of molecules from the cell membrane to the endoplasmic reticulum (ER), passing if necessary via the Golgi apparatus. This mechanism has been demonstrated for certain classes of proteins of the endoplasmic reticulum carrying the tetrapeptide KDEL (SEQ ID NO:8) at the carboxy terminal (or HDEL (SEQ ID NO:9) in starch). A great deal of biochemical and morphological evidence indicates that those proteins leave the endoplasmic reticulum, reach the Golgi apparatus in which modifications are made to their carbohydrate chain and are then redirected to the endoplasmic reticulum. The tetrapeptide KDEL (SEQ ID NO:8) is a retention signal which traps the peptide or protein to which it is attached in the endoplasmic reticulum, such trapping taking place by interaction at a receptor protein for the KDEL (SEQ ID NO:8) motif described by Lewis M. J. et al in Nature, 348 (6297): 162: 3, Nov. 8, 1990.

Other evidence for the existence of intracellular retrograde transport arises from a study of certain bacterial toxins which enter the cytosol of eukaryotic cells after passing into the endoplasmic reticulum (Pelham et al (1992) Trends cell. Biol., 2: 183–185). A particular example which has been studied is that of the Shiga toxin from Shigella dysenteriae, also E. coli Shiga-like toxins. Such toxins are composed of two polypeptide chains; one (the A fragment) is the toxic fragment and carries a deadenylase activity which inhibits protein synthesis by acting on the 28S ribosomal RNA, while the other sub-unit (the B fragment) enables the toxin to bind to the target (O'Brien et al (1992), Curr. Top. Microbiol. Immunol. 180: 65–94). Electron microscope studies have shown that Shiga toxin can be detected in the ER of A431, Vero, and Daudi cells in particular (Sandvig et al, 1992 and 1994; KHINE, 1994). Further, treating cells with a fungal metabolite which cause the loss of the Golgi apparatus structure (brefeldin A) protects the cells against Shiga toxin thus suggesting that they traverse the Golgi apparatus before reaching the ER. Finally, Kim et al (1996) have confirmed that the B fragment of the toxin is localised in the Golgi apparatus.

The following references demonstrate the state of the art as regards retrograde transport, in particular transport of the B fragment of Shiga toxin in the ER: Sandvig et al (1992), Nature 358:510–512; Sandvig et al (1994) J. Cell. Biol 126: 53–64; Kim et al (1996) J. Cell. Biol 134: 1387–1399.

Intracellular transport is defined as the ensemble of exchanges between the different cellular compartments.

The authors of the present application have observed that the B fragment is not only moved towards the ER, but also to the nucleus of hematopoietic lines, in particular dendritic cells and macrophages.

The authors have shown that those cells, incubated in the presence of two micromoles of BGly-KDEL (SEQ ID NO:8) fragment, as described below, for 3 hours then fixed, have a reactivity with specific antibodies against the toxin in the nucleus and even in the nucleole of such cells (unpublished results) which clearly indicate the existence of intracellular transport of that fragment.

The present invention results from observations on intracellular transport of the B fragment of Shiga toxin (B fragment) and uses its routing properties to construct a chimeric polypeptide sequence containing:

either a peptide or a polypeptide of therapeutic significance bound to said fragment or any functional equivalent thereof;

or a polynucleotide sequence carrying a sequence the expression of which is desired. The B fragment and the polynucleotide sequence are coupled using any technique which is known to the skilled person and in particular that described by Allinquant B. et al in the Journal of Cell Biology 1288 (5): 919–27 (1995).

In addition to covalent coupling of DNA molecules or other molecules to the B fragment, coupling can be via a strong non covalent interaction. To this end and by way of example, the cDNA of the B fragment is fused with that of streptavidin or with any other avidin derivative using known methods (Johannes et al (1987), J. Biol. Chem., 272: 19554–19561).

The protein resulting from fusion (B-streptavidin) can react with biotinylated DNA obtained by PCR using biotinylated primers, or with any other biotinylated substance. The resulting complex is bound to target cells and should be transported like the intracellular B fragment.

A further coupling method employs site-specific biotinylation of the B fragment. To this end, the cDNA of the B fragment is fused with cDNA coding for the BirA enzyme recognition site (Boer et al (1995), J. Bacteriol, 177: 2572–2575; Saou et al (1996) Gene, 169: 59–64). After in vitro biotinylation, the B fragment is bound to other biotinylated molecules (such as cDNA, see above) via streptavidin or any other tetravalent avidine derivative.

The term "functional equivalent" means any sequence derived from the B fragment by mutation, deletion or addition, and with the same routing properties as the B fragment.

More precisely, a functional equivalent can be constituted by any fragment with the same retrograde transport properties and even intracellular transport to the nucleus as those described for the B fragment. Examples which can be cited are the B fragment of verotoxin described in the Proceedings of the National Academy of Sciences of the United States of America, 84 (13): 4364–8 1987, July, or the B fragment from ricin described by Lamb F. I. Et al in the European Journal of Biochemistry, 148(2): 265–70 (1995). After describing the particular transport properties of such fragments, the skilled person will be able to select the fragment which would be the best candidate as a vector for routing any sequence in any cellular compartment.

Thus the present invention encompasses the use of the B fragment of Shiga toxin or any other sub unit of bacterial toxins which would have comparable activities, in particular routing properties analogous to those of fragment B, including polypeptides miming the Shiga toxin B fragment. These polypeptides, and in general these functional equivalents, can be identified by screening methods which have in common the principle of detecting the interaction between random peptide sequences and the $Gb_3$ receptor or soluble analogues of the receptor. By way of example, phage libraries expressing random peptide sequences for selection on affinity columns comprising $Gb_3$ or after hybridisation with soluble radioactive $Gb_3$ analogues can be used. The glycolopid $Gb_3$ has been identified as being the cellular receptor of the Shiga toxin (Lingwood (1993), Adv. Lipid Res., 25: 189–211). $Gb_3$ is expressed by cells which are sensitive to the toxin and internalisation of the toxin would be permitted by an interaction with $Gb_3$. The present inventors have demonstrated that in HeLa cells in which expression of the Gb$_3$ receptor has been inhibited (FIG. 1A), the internalised B fragment is not transported into the Golgi apparatus but is accumulated in vesicular structures in the cytoplasm, principally represented by lysosomes. In the control cells, the B fragment is transported to the Golgi apparatus (FIG. 1B).

Figure 2:
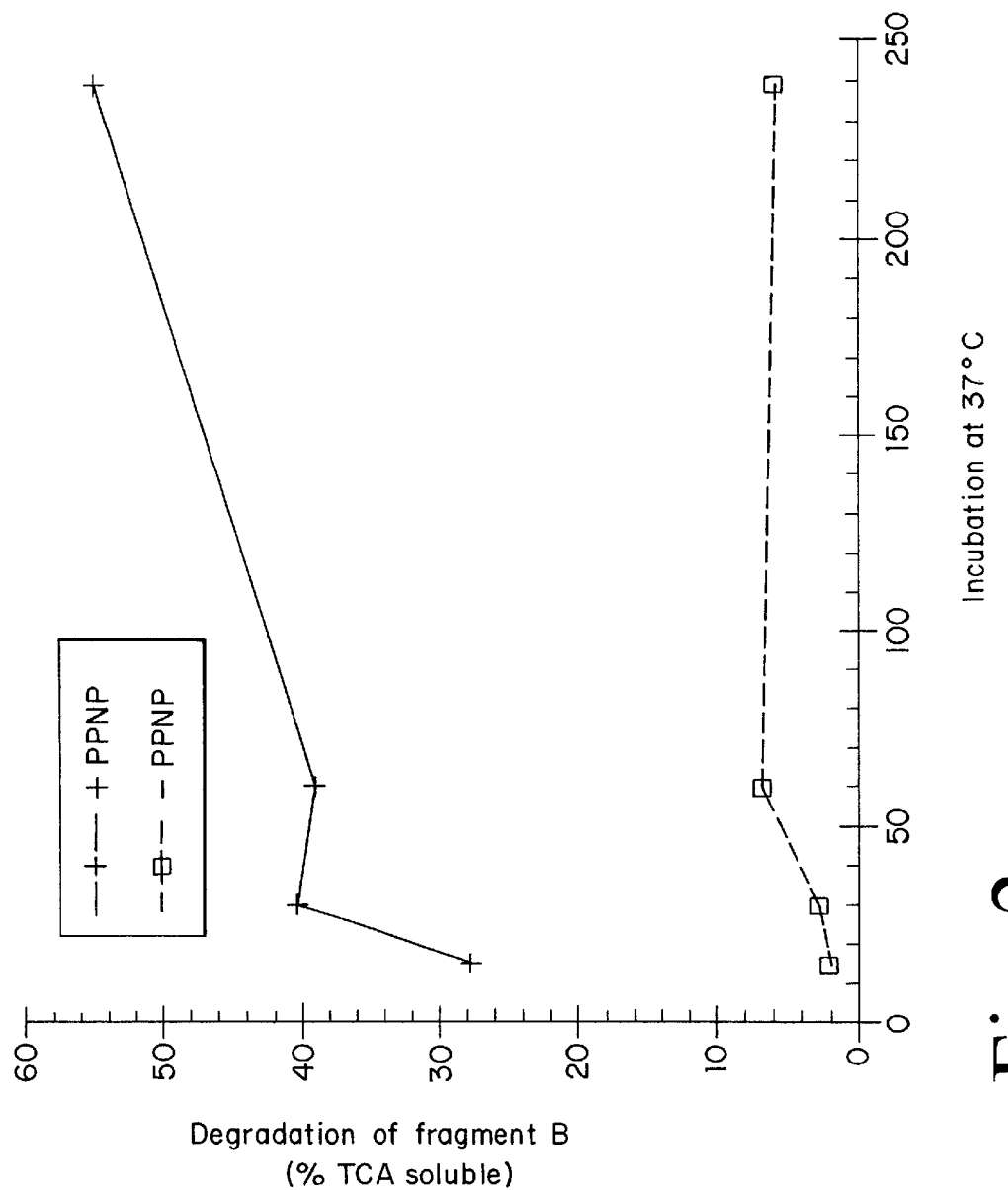

This hypothesis, whereby in the absence of the Gb$_3$ receptor, the B fragment is no longer transported to the biosynthesis system or secretion system, has been confirmed by biochemical experiments (FIG. 2).

The inventors have demonstrated that in the presence of an inhibitor of Gb$_3$ receptor synthesis, PPNP (+PPNP), up to 50% of the internalised B fragment is degraded in the form of TCA-soluble material, which conforms to a transport activity towards a subsequent degradation compartment such as an endosomal or lysosomal compartment. When Gb$_3$ receptor synthesis is not inhibited (−PPNP), a much smaller proportion of internalised B fragment becomes TCA soluble. It can thus be concluded that the presence of the Gb$_3$ receptor is necessary for addressing the B fragment to specific compartments, which tends to favour the fact the main factor in the activity of the B fragment is its binding to the Gb$_3$ receptor.

The present invention provides chimeric polypeptide sequences, said sequences comprising at least: the Shiga toxin B fragment or a functional equivalent thereof the carboxy-terminal end of which has bound to it one or more X polypeptides with the following formula:

B—X, wherein:

B represents the B fragment of a toxin such as the Shiga toxin, the sequence of which has been described by N. G. Seidah et al (1986), J. Biol. Chem. 261: 13928–31, and in Strockbine et al (1988), J. Bact. 170: 1116–22, or a functional equivalent thereof, or from verotoxin or from ricin (references supra);

X represents one or more polypeptides the upper limit to the total length of which being that of compatibility with retrograde or intracellular transport.

The present invention also provides chimeric molecules with the following structure:

BX' where B has the same meaning as above and X' represents a nucleotide sequence coding for a peptide sequence X the expression of which is desired, in particular an antigen epitope.

The chimeric molecules of the invention can also comprise:

a) modification sites such as an N-glycosylation site constituted by about 20 amino acids, phosphorylation sites or any sequence necessary for any maturation of the molecule;

b) a retention signal of the tetrapeptide KDEL type (Lys-Asp-Glu-Leu) (SEQ ID NO: 8) which, when it is bound to the carboxy-terminal end of resident ER proteins, causes retention after maturation of the proteins by passage into the Golgi apparatus. A discourse on the role of the retention signal in protein maturation has been provided by M. J. Lewis et al, (1992), cell, 68:

More generally, the chimeric polypeptide sequences can comprise:

any sequence necessary for maturation of the protein in a suitable cellular system;

any sequence necessary for recognition of a given cell type by the chimeric molecule, thus enabling selectivity of action and penetration into the cell cytoplasm.

The common factor between all chimeric sequences with structure B—X or B—X' is that they contain the B fragment or a functional equivalent thereof.

The chimeric molecules of the invention enable X sequences or the expression product of X' to be routed in the ER. When X is bound to the B fragment, retrograde transport also occurs via the Golgi apparatus and probably via the endosomes. Further, under certain conditions, the molecules of the invention can undergo maturation leading to a membrane presentation of certain epitopes contained in the chimeric polypeptide sequence.

The term "maturation" means any process which, from a given polypeptide, leads to the emergence of peptides which themselves can be presented in a cellular compartment including the cytoplasm. Maturation can occur either by enzymatic clipping in the endoplasmic reticulum, or by transport into the cytoplasm in which the polypeptide is cleaved then the peptides obtained are again transported in the endoplasmic reticulum.

Molecules of the class I major histocompatibility complex (c1 I MHC) can become charged with polypeptide molecules of interest X or X' after such cleavage and be presented on the cellular membranes.

When the chimeric molecule of the invention consists of coupling a B fragment or its equivalent with a polynucleotide molecule or an expression vector comprising a sequence the expression of which is desired, after transcription in the nucleus then translation in the cytoplasm, the polypeptide which is synthesised can undergo the same steps of cleavage, maturation and intracellular transport as that described above for a polypeptide chimeric sequence.

Chimeric polypeptide molecules in accordance with the invention can constitute an active principle in a therapeutic composition for immunotherapy by a mechanism which is close to biological processes regarding antigen presentation suitable for development of the immune reaction. The X fragment thus represents one or more epitopes for which membrane presentation is desired at the cell surface. The size of the X fragment is limited only by the intracellular transit capacity of the chimeric molecules under consideration.

This approach can be envisaged both for an anti-infectious or an anti-cancer immunotherapy and for constituting an antigenic bait in certain autoimmune diseases.

Any type of antigen presented by c1 I MHC is a good candidate for selecting simple or chimeric epitopes which form part of the constructions of the invention. Examples which can be cited are:

a) Human epitopes derived from melanoma cell proteins:
  BAGE from tyrosinase (Boel, P et al (1995), Immunite 2, 167–75);
  GAGE from gp75 (Van den Eynde, B. et al (1995), J. Exp. Med. 182, 689–98);
  tyrosinase (Brichard V. et al (1993), J. Exp. Med. 178, 489–95);
  p15 from A/MART-1 melanoma (Coulie P. G. et al (1994), J. Exp. Med. 180, 35–42; Kawakami Y. et al (1994), J. Exp. Med. 180, 347–52);
  MAGE-1 and -3 from β-catenin (De Plaen E. et al (1994), Immunogenetics 40, 369–9; Traversari C et al (1992), J. Exp. Med. 176, 1453–7.

b) Human enitopes derived from virus proteins involved in cancer development:
  Peptides derived from E6 and E7 proteins of HPV 16 (Feltkamp M. C. et al (1993), Eur. J. Immunol. 23, 2242–9; Davis H. L. et al (1995), Hum. Gene Ther. 6, 1447–56);

Peptides derived from the Hbs protein of HBV (Rehermann B. et al (1995), J. Exp. Med. 181, 1047–58);

Peptides derived from proteins from EBV (Murray R. J. et al (1992), J. Exp. Med. 176, 157–68);

Peptide derived from cytomegalovirus.

c) Human epitopes derived from oncogenes:

p21ras (Peace D. J. (1993), J. Immunother 14, 1104; Ciemik, I. F. et al (1995) Hybridoma 14, 139–42);

p53 (Gnjatic S. (1995), Eur. J. Immunol. 25, 1638–42).

d) Epitopes of interest in autoimmune diseases:

These epitopes can be selected from those described by Chiez, R. M. et al (1994) in Immunol. Today 15, 155–60.

e) Epitopes of interest in infectious diseases:

Examples of such epitopes which can be cited are those described by Furukawa K. et al (1994) in J. Clin. Invest. 94, 1830–9.

In the constructions of the invention, X or the expression product of X' can also represent a polypeptide sequence which can restore an intracellular transport function which has been perturbed by whatever cause. As an example, a biological molecule can be trapped in the ER due to a modification by mutation, deletion or addition of a sequence, having the effect of blocking maturation or transit of that molecule. This is the case, for example, with mutated CFTR (ΔF508) where binding to a chaperone molecule such as calnexin is modified such that its release is prevented or retarded, thus preventing intracellular transit. This mutation is the cause of cystic fibrosis. Introducing a non mutated replica into the endoplasmic reticulum could displace N-glycosylated chains of the CFTR (ΔF508) glycoprotein from the interaction site with calnexin, with the result that protein transport to the plasma membrane is renewed, and the epithelial cells of the lung function normally.

The invention also provides nucleic acid constructions, in particular DNA or cDNA comprising a sequence of nucleotides coding for the chimeric protein the structure and variations of which have been defined above. More particularly, the invention provides expression vectors or plasmids carrying the above constructions and capable of being expressed in bacterial cultures. By way of example, the expression vector can be the pSU108 plasmid described by G. F. Su et al (1992), Infect. Immun. 60: 3345–59.

More particularly, the invention provides constructions comprising:

the sequence coding for the B fragment;

a sequence coding for one or more polypeptides the expression of which is desired. These may be epitopes the membrane expression of which is desired at the cell surface; they may also be polypeptides which can retain proteins in the Golgi apparatus; finally, they may be polypeptides which can restore a disturbed intracellular transport function.

The construction can also comprise any nucleic acid sequence coding for a polypeptide the presence of which enables proper intracellular transport in cells intended to be treated by the molecules of the invention. In particular, it may be:

a sequence coding for an N-glycosylation signal;

a sequence coding for the KDEL (SEQ ID NO: 8) retention signal.

The polynucleotide constriction of the invention is under the control of a promoter, preferably a strong promoter which can produce the correct degree of expression in bacteria into which it has been transfected.

The invention also provides transfected bacteria comprising these constructions, and capable of producing the chimeric polypeptides or proteins of the invention.

The host cells treated by the molecules of the invention also form part of the invention; they may be any type of cell, in particular:

those which can be treated in vivo such as immune system cells which are active in triggering cellular immunity, such as dendritic cells, macrophages or B lymphocytes;

those which can be treated in situ such as epithelial cells for use in restoring functions which have been altered either by a genetic defect or by a metabolic perturbation; cancer cells.

In general, the chimeric molecules of the invention allow a novel therapeutic method to be postulated which can overcome the problems linked to viral vectors or retroviral vectors which are normally used to integrate and express exogenous molecules in animal cells. The therapeutic method which derives from the molecules of the invention consists of directly treating the cells of a patient, either ex vivo or by direct stereotaxic application with the chimeric polypeptide sequences, or by conventional mucosal treatment methods such as aerosols.

The invention concerns the use of chimeric polypeptide or polynucleotide sequences coding for the polypeptides of the Livention in the production of therapeutic compositions in which particular polypeptides are expressed in the membranes of target cells. These polypeptides are advantageously epitopes against which the development of an immunological reaction is desired which are then presented on the surface of the immune system cells, in particular dendritic cells, macrophages or B lymphocytes. The B fragment of the Shiga toxin acts as an epitope vector enabling cells presenting antigens to be programmed.

The present invention concerns an immunotherapeutic method consisting of increasing cellular immunity as the result of the presence of an undesirable antigen in an organism, said method consisting of causing key cells of the immune system, such as dendritic cells and macrophages, to express particular epitopes. The treatment method of the invention is aimed at triggering immunity to cellular and humoral mediation by charging the cl I or cl II MHC molecules with the epitopes of interest, after restriction in the target cells. This leads to activation of cytotoxic T cells against the antigen which it is desired to eliminate.

The epitopes presented through the constructions of the invention originate from viral, parasitic or bacterial antigens or from any cell, organite, or micro-organism the elimination of which is desired, such as cancer cells or infected cells. The epitopes can also act as bait enabling "self" molecules recognised as foreign antigens in autoimmune diseases to be replaced by the epitopes of the invention, thus slowing down or reducing the immune reaction.

Examples of these epitopes have been cited above in the description of the chimeric polypeptide sequences.

The invention also concerns the use of the chimeric molecules of the invention in the manufacture of therapeutic compositions in which the particular polypeptides which it is desired to express can restore intracellular transit of a protein the altered structure of which leads to it being trapped in the ER and to an expression deficit. This is the case for membrane expression proteins which undergo intracellular maturation, including glycosylations, sulphatations, folding etc.

A particular example is that of mutated CFTR (ΔF508) wherein the attachment of a chaperone molecule such as calnexin is modified following modification of the protein; this leads to the molecule being trapped, causing cystic fibrosis, leading to a general insufficiency of exocrin secretions, in particular in the pancreas and lungs.

The present invention concerns a therapeutic treatment method for diseases having an origin in a fault in protein secretion; the method consists of directly administering the chimeric polypeptides or administering the genetic information to the cells of patients in the form of plasmids carrying exogenic sequences coding for a peptide or polypeptide which can restore the deficient cellular function.

This restoration can result either in supplementation of the deficient function by the polypeptide X or competition between the mutated protein and the polypeptide synthesised from the exogenic sequence for binding with a specific molecule or receptor of the cellular machinery. A particular example is the treatment of the mutant cited above, causing cystic fibrosis, by administering a vector carrying a sequence coding for the attachment site for the CFTR protein with its chaperone molecule or by direct administration of the chimeric polypeptide.

The constructions of the invention endow the human or animal health world with a novel therapeutic means for treating diseases caused by a deficit in intracellular transit or for increasing or inducing a membrane presentation of a molecule, a polypeptide or an epitope of interest.

Further properties of the invention will become clear from the following examples and figures.

KEY TO FIGURES

Figure 1B:
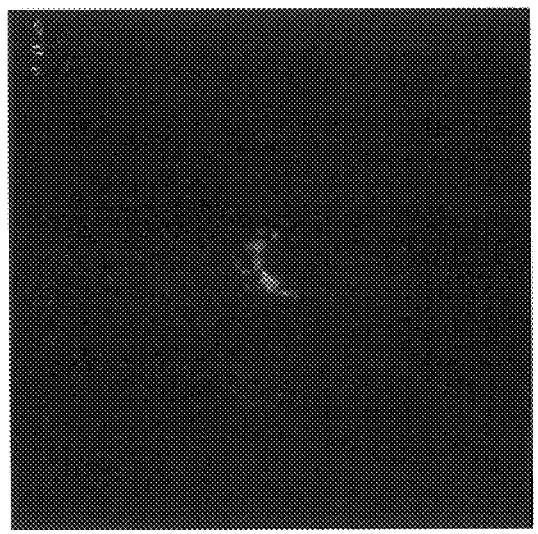

FIG. 1A: HeLa cells in which expression of the $Gb_3$ receptor has been inhibited. The internalised B fragment is not transported to the Golgi apparatus but is accumulated in the vesicular structures.

FIG. 1B: Control HeLa cells in which the B fragment is transported to the Golgi apparatus.

FIG. 2: Biochemical test showing the defect in B fragment transport.

Figure 3:
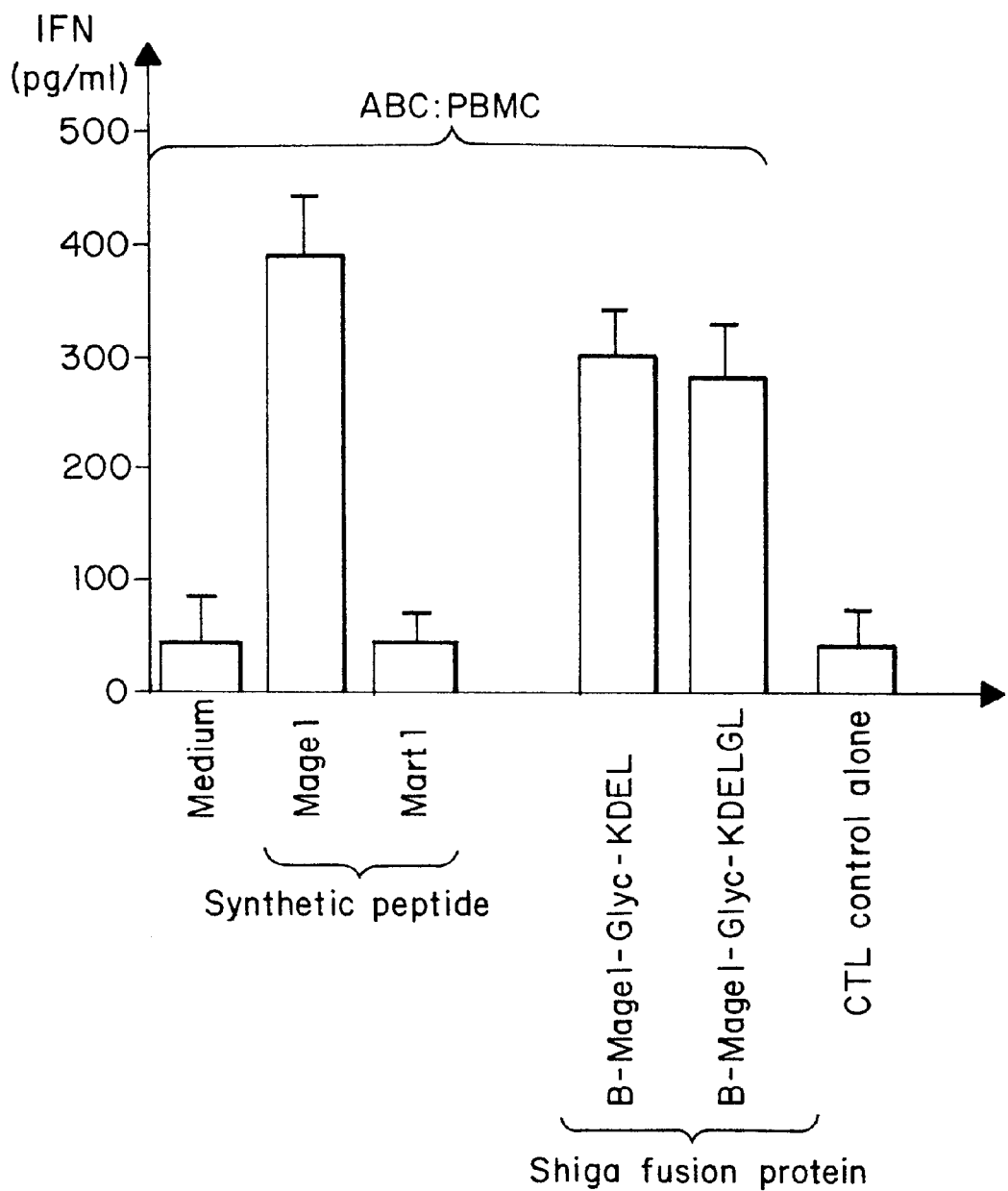

FIG. 3: MHC class I restricted presentation of Shiga B-Mage 1 fusion proteins at peripheral blood monocytic cells (PBMC): role of the KDEL (SEQ ID NO:8) sequence. The PBMC ($5 \times 10^4$) were primed overnight with either Mage 1 peptide (1 μM) or Mart 1 peptide (1 μM) or Shiga B-Mage 1 fusion proteins (1 μM) with a sequence which is active (B-Mage 1 -Glyc-KDEL (SEQ ID NO:8)) or inactive (B-Mage 1 -Glyc-KDELGL) (SEQ ID NO:10) for recycling to the endoplasmic reticulum. After washing, $2 \times 10^4$ cytotoxic T cells specific for the Mage 1 epitope (clone 82/30) were incubated with PBMC cells primed for 24 hours. The supernatants were then collected and tested for the production of γ interferon.

Figure 4:
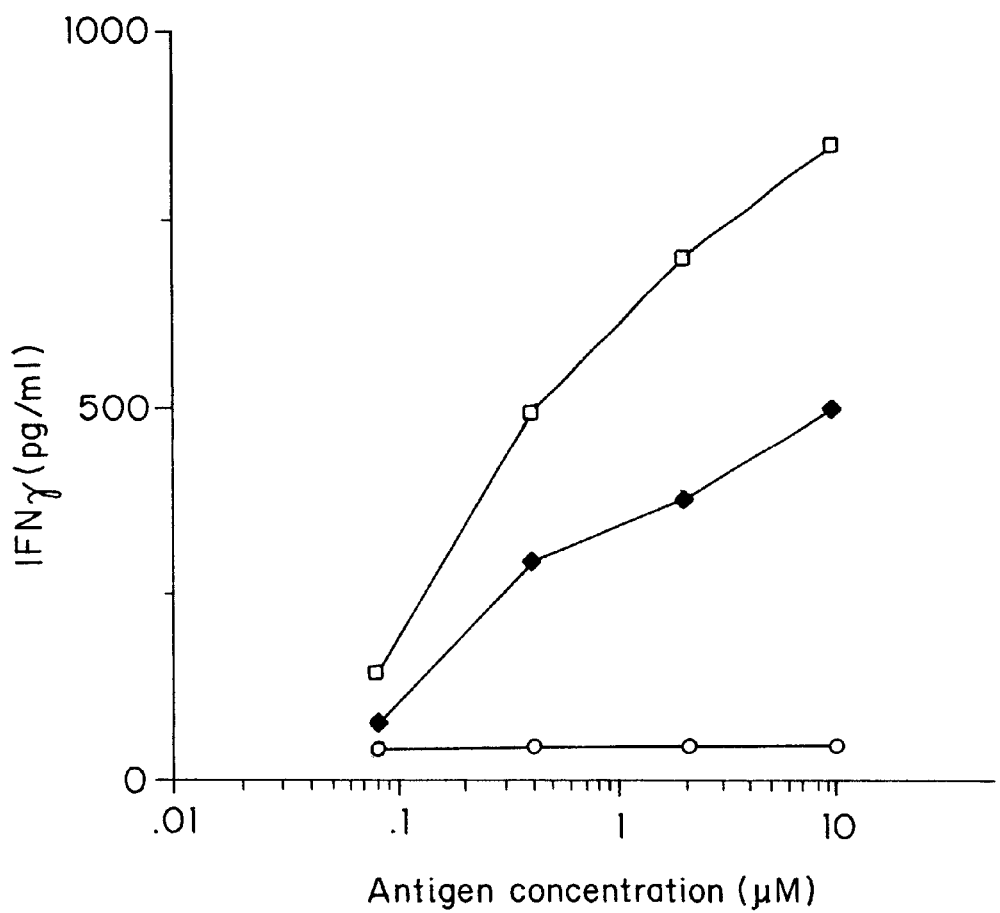

FIG. 4: MHC class I restricted presentation of the Shiga B-Mage 1 fusion protein by different types of cells presenting antigens. B lymphoblastoid cells ▫, dendritic cells (+) or clonal T cells ▨ were primed with the soluble Shiga B-Mage 1 fusion protein, as for FIG. 3. Presentation of Mage 1 peptides was tested using the 82/30 CTL line.

Figure 5:
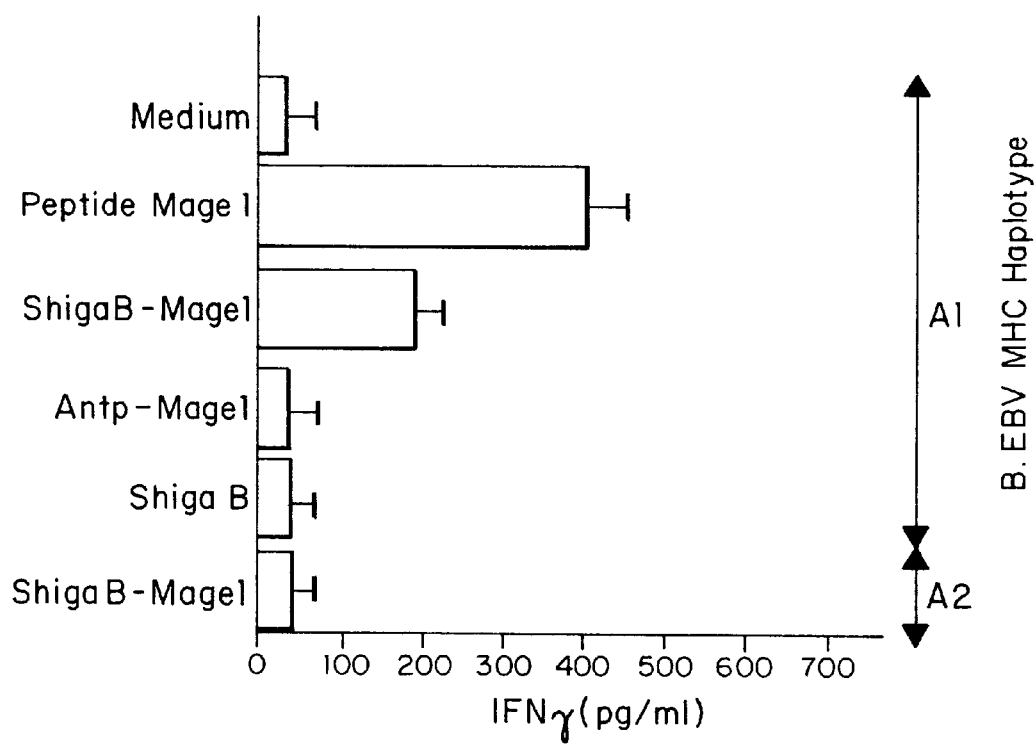
Figure 5:
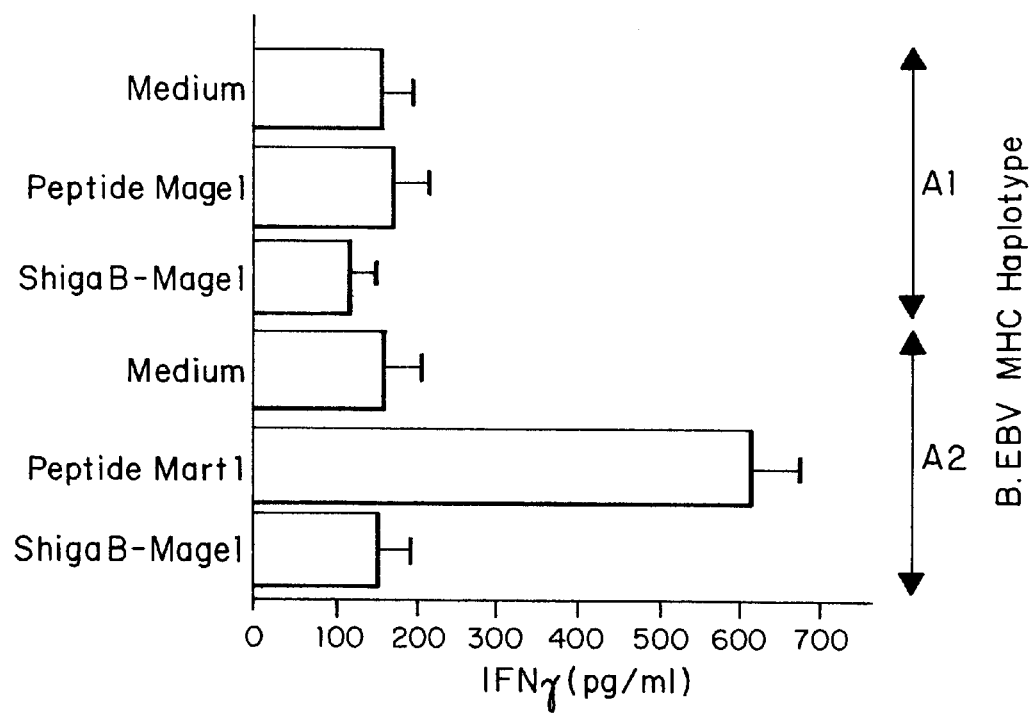

FIG. 5: Analysis of the specificity of the MHC class I restricted presentation of the Shiga B-Mage 1 fusion protein by lines of B lymphoblastoid cells. Cells from the BM21 (HLA-A1) or BV1 (HLAA2) B lymphoblastoid line were primed overnight either with medium alone or with Mage 1 or Mart 1 synthetic peptides (1 μM), or with Shiga B-Mage 1 fusion protein (1 μM), or with Anti-Mage 1 fusion protein or with the B fragment of wild-type Shiga toxin. After washing, specific cells of Mage 1 TCL 82/30 (A) or Mart 1 CTL LB373 (B) were incubated for 24 hours with primed B-EBV cells. The supernatants were then collected and tested for the production of γ interferon.

I—CONSTRUCTION OF A RECOMBINANT CHIMERIC POLYNUCLEOTIDE AND THE PRODUCTION OF THE CORRESPONDING PEPTIDE

I—1) Construction of Plasmid

The X epitope selected was the MAGE epitope, present in cancer cells of patients with melanoma. The plasmid used was the pSU108 plasmid described by Su et al, 1992, Infect. Immun. 60: 33–45, 3359.

The PCR primers used were as follows:

5'-ACTAGCTCTGAAAAGGATGAACTTTGAGAA TTCTGACTCAGAATAGCTC-3' SEQ ID NO. 1)

5'-CTTTTCAGAGCTAGTAGAATTAGGATGATAGCG GCCGCTACGAAAAATAACTTCGC-3'(SEQ ID NO. 2)

The primers were used with specific primers from the ShigaAtpE (5') vector

5'-CACTACTACGTTTTAAC-3'(SEQ ID NO. 3)

5'-CGGCGCAACTATCGG-3'(SEQ ID NO. 4) to produce fragments which were cloned at the restriction sites SphI and SaII of the SU108 plasmid.

Adapter fragments containing the glycosylation site and the KDEL sequence composed of the oligonucleotides sulphate 1: ((5'-phosphorylated; 5'-GGCCGCCATCCT AATTCTACTTCT-3')(SEQ ID NO. 5) and sulphate 2 (5'-CTCAGAAGTAGAATTAGGATGGC-3')(SEQ ID NO. 6) or sulphate 3 (5'GAGTCTGAAAAAGATGAACT TTGATGAG-3')(SEQ ID NO 7) were ligatured overnight at 16° C.

The resulting fragments were cloned at the NotI and EcoRI restriction sites of pSU108 and containing the cDNA coding for B-Glyc-KDEL (SEQ ID NO:8) cells to presentation of membrane epitopes. This mixture was incubated at 30° C. for 4 hrs. DCs which had internalised the B fragment coupled to this epitope were irradiated at 5000 rad, assembled by centrifuging, taken up into suspension, and mixed with CD8+ lymphocytes (prepared from PBMC). These DC, pulsed with an antigen, and the CD8+ were then kept in co-culture in the presence of 5 ng/ml of IL-7.

The recombinant fragments were also purified using the technique described by Su et al, 1991, cited above. In brief, E. coli cells containing recombinant expression plasmids obtained from pSU108 were cultured overnight at 30° C. The culture was then diluted 5 times in LB supplemented with 50 mg/ml of ampicillin, at 50° C. After incubation for 4 hours at 42° C., the cells were thoroughly washed with 10 mM Tris/HCL, pH 8, incubated for 10 minutes in 10 mM Tris/Hcl, pH 8; 25% sucrose, 1 mM EDTA, and finally rapidly re-suspended in a water-ice mixture containing 1 mM of PMSF and a protease inhibitor mixture (leupeptin, chymostatin, pepstatin, antipain and aprotinin). The final step led to rupture of the periplasm. After clarification, the supernatant was charged onto a QFF column (Phannacia) and eluted with a linear gradient of NaCl in 20 mM Tris/HCl, pH 7.5. depending on the construction, the B fragment was eluted between 120 mM and 400 mM. The fractions containing the B fragment were then dialysed against 20 mM of Tris/HCl, pH 7.5, and re-charged onto a monoQ column (Pharmacia) and eluted in the same manner as before. The resulting proteins, estimated to have a degree of purity of 95% using polyacrylamide-SDS gel electrophoresis, were then stored at −80° C. until use.

I—3) Induction of a CTL Response In Vitro

Dendritic cells (DC) were cultured using previously established protocols (Romani et al, 1994). Briefly, PBMC were taken up into suspension in Iscove medium and incubated for 2 h at 37° C. in 6-well trays. Cells which had not adhered were removed and the remaining cells were incubated at 37° C. in the presence of GM-CSF (800 U/ml) and IL-4 (500 U/ml). After 5 days culture, the IL-1α and IFN-γ in respective concentrations of 50 U/ml and 150 U/ml were added and incubation was continued at 30° C. for 24 h. The dendritic cells were then taken up into suspension in Iscove medium in the presence of increasing concentrations of B fragment coupled with the MAGE epitope and in the presence of 3 μg/ml of human β2-microglobulin to improve the capacity of the cells to presentation of membrane epitopes. This mixture was incubated at 30° C. for 4 hrs. DCs which had internalised the B fragment coupled to this epitope were irradiated at 5000 rad, assembled by centrifuging, taken up into suspension, and mixed with $CD8^+$ lymphocytes (prepared from PBMC). These DC, pulsed with an antigen, and the $CD8^+$ were then kept in co-culture in the presence of 5 ng/ml of IL-7.

After 10 days, responsive $CD8^+$ lymphocytes were re-stimulated by freshly prepared irradiated DCs which were then also incubated in the presence of increasing concentrations of fragment B coupled to the same epitope. The co-culture of DC and responsive $CD8^+$ lymphocytes was continued in the presence of IL-2 and IL-7 in concentrations of 10 U/ml and 5 ng/ml respectively. This re-stimulation protocol was repeated 3 times.

In order to measure the introduction of a CTL response, responsive $CD8^+$ lymphocytes pre-stimulated as described above were incubated in the presence of cancer cells or cells infected with a virus. These cells, which expressed the selected epitope, were labelled with $Na_2{}^5CrO_4$ then brought into contact with responsive $CD8^+$ for 5 hours (Bakker et al, 1994). The radioactivity released in the medium was then determined, enabling the cytotoxic activity of the pre-stimulated responsive $CD8^+$ lymphocytes to be quantified.

Results

II—PRESENTATION OF THE MAGE 1 ANTIGEN BY PENA-EBV CELLS AND DENDRITIC CELLS PULSED BY A B FRAGMENT OF THE SHIGA TOXIN CARRYING THIS ANTIGEN.

II—1) Morphological Study of Intracellular Transport of a B Fragment Carrying the MAGE- 1 Epitope We have demonstrated that it is possible to fuse a peptide sequence to the carboy-terminal end of the Shiga toxin B fragment while retaining intracellular routing of this protein towards the endoplasmic reticulum (ER). This demonstration was carried out by constructing chimeric polypeptides comprising the B fragment, the N-glycosylation site and the KDEL (SEQ ID NO: 8) retention signal. As a control, the KDELGL (SEQ ID NO:10) retention signal was used, namely the inactive version of the KDEL (SEQ ID NO:8) peptide, Misendock and Rothman, 1995, J. Cell. Biol. 129: 309–319. Morphological and biochemical studies have shown that the modified B fragment is transported from the plasmid membrane via the endosomes and the Golgi apparatus to the endoplasmic reticulum. This transport is inhibited by BFA (brefeldin A fungal metabolite) and reduced by nocodazole (a microtubule depolymerisation agent).

These experiments clearly demonstrate that intracellular routing of the fusion protein towards the endoplasmic reticulum was retained. To evaluate the potential of the B fragment as an epitope vector for anti-tumoral vaccination in vitro, the MAGE- 1 epitope was added to the B-GlycKDEL (SEQ ID NO:8) fragment under the experimental conditions described above. The novel protein was designated B-MAGE-Glyc-KDEL (SEQ ID NO:8). The B-MAGE-Glyc-KDEL (SEQ ID NO:8) protein was coupled with the fluorophore DTAF in order to follow its intracellular transport by confocal microscopy. After internalistion, this protein was detectable in the Golgi apparatus and in the ER of HeLa cells and Pena-EBV cells (a B lymphocyte line immortalised using the Epstein-Barr virus). These results confirm the original observations concerning the intracellular transport of the B fragment modified at its carboxy-terminal end (described above) and affirm that certain presenting cells of the hematopoietic line are capable of internalising the B fragment and transporting the protein to the ER.

We shall now describe these studies measuring the N-glycosylation of the B-MAGE-Glyc-KDEL (SEQ ID NO:8) protein. N-glycosylation is a modification which is carried out specifically in the ER, and we have demonstrated above that a B fragment carrying a recognition site for N-glycosylation is in fact glycosylated if it is transported to the ER.

II—2) STUDY OF THE PRESENTATION OF THE MAGE-1 ANTIGEN BY PENA-EBV CELLS AND DENDRITIC CELLS PULSED BY THE B-MAGE-GLYC-KDEL (SEQ ID NO:8) PROTEIN.

In order to evaluate the capacity of the fragment to act as an epitope vector, we use cytotoxic T lymphocyte clone (CTL 82/30) specifically recognising the MAGE-1 epitope associated with MHC class I of cells presenting the HLA-A1 haplotype. These CTL were kept in the presence of Pena-EBV cells or dendritic cells pulsed with the B-MAGE-Glyc-KDEL (SEQ ID NO:8) protein. If the MAGE-1 epitope is presented by presenting cells, the CTL will be activated and will secrete γ interferon which (IFNγ) which is then assayed.

The quantity of IFNγ secreted is proportional to the amplitude of the stimulation of the CTLs by the presenting cells.

Presenting cells (Pena-EBV and dendritic, 20000 cells per round bottom microwell) were either fixed for 1 h with 4% PBS-paraformaldehyde, or were not fixed. They were than washed twice with OptiMEM before being incubated for 15 h with dilutions of the B-MAGE-Glyc-KDEL (SEQ ID NO:8) protein. The protein was tested at 4 dilutions, starting with a concentration of 10 μmM final, and diluting 5 in 5 in the OptiMEM medium (medium without serum). After 15 h, the plates were washed twice by low speed centrifuging. The CTL (CTL 82/30) were added in an amount of 5000 CTL per well in 100 μl of culture medium (ID-HS-AAG +25 U/ml of IL2). As a positive control, some CTL 82/30 were kept in the presence of line G43 (a B lymphocyte line transfected with an expression plasmid of MAGE-1). After 24 h of incubation, the supernatants were harvested to determine the quantity of IFNγ produced. The results are shown in Table I.

TABLE I

| | Concentration of B-MAGE-Glyc-KDEL (SEQ ID NO:8) | | | |
|---|---|---|---|---|
| Cell type | 10 μM | 2 μM | 0.4 μM | 0.08 μM |
| Dendritic | | | | |
| Fixed | 446 ± 293 | 821 ± 64 | 661 ± 18 | 312 ± 181 |
| Non fixed | 1557 ± 404 | 1315 ± 91 | 1232 ± 150 | 1174 ± 478 |
| Pena-EBV | | | | |
| Fixed | 70 ± 47 | 68 ± 48 | 23 ± 32 | 4 ± 5 |
| Non fixed | 1966 ± 415 | 1960 ± 206 | 1544 ± 42 | 853 ± 116 |

The results are represented by the amount of IFNγ produced under each set of conditions (average±standard deviation; n=3).

We can see that the dendritic cells and the Pena-EBV cells pulsed with the B-MAGE-Glyc-KDEL (SEQ ID NO:8)

protein were properly recognised by the CTL, even at low concentrations of the protein. In contrast, the dendritic cells and the Pena-EBV cells which had been previously fixed were not recognised. It thus appears that endocytosis and processing of the B-MAGE-Glyc-KDEL (SEQ ID NO:8) protein had taken place. These encouraging results will now be backed up by in vitro vaccination experiments.

III—IN VIVO ANTI-TUMORAL AND/OR ANTIVIRAL ACTIVITY TEST IN THE MOUSE

Mouse dendritic cells were prepared and marked with an antigen derived from P21RAS, P53 or EP2/NER proteins to test the anti-tumoral activity, or HBV, EBV or HPV to test antiviral activity. This preparation of dendritic cells was carried out using the protocol described in I-4) above.

These dendritic cells were then introduced into the mouse.

The antiviral or anti-tumoral effect was observed by subsequent treatment of these mice grafted with tumoral cells or virus expressing this antigen.

Conclusion

The polypeptide sequences or polynucleotide sequences of the invention can thus advantageously constitute an active principle in a pharmaceutical composition intended for the treatment of certain cancers or certain viral or bacterial infections, from the moment when a particular epitope of said virus or said cancer cell will have been integrated into the recombinant nucleotide sequence, leading to synthesis of a chimeric polypeptide which can be restricted by the MHC class I and can be expressed on the membrane surface of immune system cells.

IV—RESTORATION OF INTRACELLULAR TRANSPORT OF THE MUTATED PROTEIN CFTR (αF508) USING THE SHIGA TOXIN B FRAGMENT.

The CFTR (cystic fibrosis transmembrane regulator) protein is a chlorine channel of the plasmic membrane. In the large majority of patients with cystic fibrosis, the CFTR gene carries mutations. The mutation (αF508) which is the most frequently observed affects intracellular routing of the CFTR protein. In fact, the mutated protein CFTR(αF508), which is functional as regards its ionic channel activity, remains blocked at the endoplasmic reticulum, instead of being transported to the plasmic membrane. Using the Shiga toxin B fragment, we have introduced a domain of the CFTR protein which is known to be the domain of interaction with the calnexin protein (ER "chaperone") into the endoplasmic reticulum. This domain is fused to the carboxy-terminal end of the B fragment. We have tested whether this chimeric protein can displace N-glycosylated chains of the CFTR (αF508) glycoprotein from the interaction site with calnexin, with the result that the CFTR(αF508) protein is no longer retained in the endoplasmic reticulum and can be transported to the plasmic membrane and thus function normally.

Firstly, we constructed a chimeric protein composed of a B fragment and the interaction domain derived from the CFTR protein. A recycle signal (the KDEL (SEQ ID NO:8) peptide) was added to the carboxy-terminal end of this protein to increase its retention in the endoplasmic reticulum. It was first verified that the novel protein was also transported in the endoplasmic was also transported in the endoplasmic reticulum of target cells. Mobilisation of CFTR (αF508) was studied in cells of a stable cell line, LLCPK1, transfected with the cDNA of CFTR(αF508). This line was established by Mlle. M. A. Costa de Beauregard and M. D. Louvard (Institut Curie, Paris, CNRS UMR 144). The CFTR (αF508) protein which was expressed in these cells was also endowed with an epitope tag. It was thus possible to detect the arrival of the CFTR (αF508) protein in the plasmic membrane by immunofluorescence. In the absence of treatment, the plasmic membrane of LLCPKI cells of the line was depleted with specific CFTR (αF508) tags in the plasmic membrane. While the results of these pilot experiments are promising, we are obliged to develop this approach within the context of cystic fibrosis therapy.

Conclusion

The experiment described above shows that the synthetic polypeptide in which X is constituted by an interaction domain between the CFTR protein and calnexin can advantageously constitute the active principle of a therapeutic composition intended to treat cystic fibrosis. In fact, competition between the mutated interaction domain in the mutant and the fragment of synthetic polypeptide for the interaction with calnexin can restore secretion of the mutated protein in the bronchia.

Antigenic Presentation Test

Cells presenting the antigen (CMSP, B-EBV cells, T cells, dendritic cells) were incubated in 96-well microplates in a density of $10^5$ cells per well and pulsed at 37° C. for 4 hours or 15 hours with the antigen dissolved in 100 μl of Iscove medium. After incubation, the medium was removed and 20000 CTL cells were added to each well in 100 μl of CTL culture medium containing 25 U/ml of IL2. After 24 hours, 50 μl of supernatant was collected and the γ interferon was measured by an ELISA (Diaclone) test. In some experiments, the cells were fixed with 1% paraformaldehyde for 10 minutes at ambient temperature and washed thoroughly before transfer into the microplates.

What is claimed is:

1. A chimeric polypeptide of the formula:

B—X wherein

B represents the B fragment of Shiga toxin or a functional equivalent thereof, and X represents one or more polypeptides of therapeutic significance, wherein said polypeptides are compatible with retrograde transport mediated by B to ensure processing or correct addressing of X.

2. The polypeptide of claim 1, wherein said polypeptide further comprises a glycosylation site, a signal for retention in the endoplasmic reticulum, a sulphatation site, or a combination thereof.

3. The polypeptide of claim 1, wherein X is an epitope which can be presented by the class I major histocompatibility complex.

4. The polypeptide of claim 3, wherein X is an epitope of a polypeptide or a protein, wherein the expression of said polypeptide or protein is desired at the surface of cells of the immune system.

5. The polypeptide of claim 4, wherein said protein or polypeptide is a cancer cell protein, a virus protein or an oncogene.

6. The polypeptide of claim 5, wherein X is a MAGE epitope specific to melanoma cells.

7. The polypeptide of claim 1, wherein X is a polypeptide which can restore or activate an intracellular transport function by interacting with proteins of the cellular machinery, wherein said polypeptide competes in the endoplasmic reticulum with the mutated form of a protein involved in intracellular transport or by supplementing a function which is deficient in said transport.

8. The polypeptide of claim 7, wherein X is the domain of interaction of the cystic fibrosis transmembrane regulator (CFTR) protein with calnexin.

9. A therapeutic composition, comprising the polypeptide of claim 1.

10. The therapeutic composition of claim 9, wherein said composition restores deficits in intracellular transport.

11. The therapeutic composition of claim 9, wherein said composition stimulates the immune defenses of the organism towards viral, parasitic or bacterial infections or cancerous antigens.

12. The therapeutic composition of claim 9, wherein said composition reduces or prevents immune reactions in autoimmune diseases.

* * * * *

SEQUENCE LISTING

<160> NUMBER OF SEQ ID NOS: 10

<210> SEQ ID NO 1
<211> LENGTH: 49
<212> TYPE: DNA
<213> ORGANISM: Artificial Sequence
<220> FEATURE:
<223> OTHER INFORMATION: Description of Artificial Sequence: Primer

<400> SEQUENCE: 1

-continued

```
actagctctg aaaaggatga actttgagaa ttctgactca gaatagctc          49

<210> SEQ ID NO 2
<211> LENGTH: 56
<212> TYPE: DNA
<213> ORGANISM: Artificial Sequence
<220> FEATURE:
<223> OTHER INFORMATION: Description of Artificial Sequence: Primer

<400> SEQUENCE: 2
cttttcagag ctagtagaat taggatgata gcggccgcta cgaaaaataa cttcgc    56

<210> SEQ ID NO 3
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 3
cactactacg ttttaac                                              17

<210> SEQ ID NO 4
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 4
cggcgcaact atcgg                                                15

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 5
ggccgccatc ctaattctac ttct                                      24

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 6
ctcagaagta gaattaggat ggc                                       23

<210> SEQ ID NO 7
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 7
gagtctgaaa aagatgaact ttgatgag                                  28

<210> SEQ ID NO 8
<211> LENGTH: 4
<212> TYPE: PRT
<213> ORGANISM: Artificial Sequence
```

-continued

```
<220> FEATURE:
<223> OTHER INFORMATION: Description of Artificial Sequence: Primer

<400> SEQUENCE: 8

Lys Asp Glu Leu
 1

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence: Primer

<400> SEQUENCE: 9

His Asp Glu Leu
 1

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Primer

<400> SEQUENCE: 10

Lys Asp Glu Leu Asp Leu
 1               5
```